United States Patent [19]
Dean

[11] Patent Number: 4,955,394
[45] Date of Patent: Sep. 11, 1990

[54] PROTECTIVE FACE SHIELD

[76] Inventor: Glen R. Dean, 2525 N. 8th St., Suite 109, Grand Junction, Colo. 81501

[21] Appl. No.: 294,395

[22] Filed: Jan. 9, 1989

[51] Int. Cl.$^5$ .............................................. A62B 18/08
[52] U.S. Cl. ................................. 128/863; 128/206.23
[58] Field of Search ............. 128/863, 206.12, 201.15, 128/201.24, 857, 858, 206.23; 2/9, 12, 206

[56] References Cited

U.S. PATENT DOCUMENTS

| | | | |
|---|---|---|---|
| 1,564,663 | 12/1925 | Galligan | 2/13 |
| 3,991,753 | 11/1976 | Viesca y Viesca | 128/863 |
| 4,296,746 | 10/1981 | Mason, Jr. et al. | 128/206.12 |
| 4,821,340 | 4/1989 | Johnson | 2/13 |
| 4,843,643 | 7/1989 | Parissenti et al. | 2/13 |

FOREIGN PATENT DOCUMENTS 2179862  3/1987  United Kingdom ........... 128/201.24

Primary Examiner—Edgar S. Burr
Assistant Examiner—Aaron J. Lewis
Attorney, Agent, or Firm—Trask, Britt & Rossa

[57] ABSTRACT

A full-face shield having spectacle openings which mate with the rims of eyeglass spectacles is disclosed. The shield is a continuous lightweight plastic shield which has two eye socket openings which form a press fit about the external rim of the spectacles. The shield is thus held in place by its fit upon the spectacles which are then worn by a person desiring to use the shield. The shield is generally disposable when contaminated but can be sterilized and is readily removed from the spectacles, which are usually cleaned before having another fresh shield attached to them.

12 Claims, 4 Drawing Sheets

PROTECTIVE FACE SHIELD

BACKGROUND OF THE INVENTION

Face shields to protect various medical personnel, particularly dentists or medical technicians and the like, from being contacted with infectious liquids are commonly worn.

Face shields presently in existence are of several types. One type hooks onto a pair of spectacles and is a face shield for the portion of the face from the eyebrows down. Such a shield is a continuous sheet of plastic without any openings and the wearer must look not only through the lenses of the spectacles, but also through the plastic sheet Another type of shield is one which attaches to a visor which is worn with a headband, and the shield may be lowered and raised much like a welder's mask.

U.S. Pat. No. 3,991,753 to Viesca discloses a face shield which is a continuous sheet of plastic without any openings in it which has attachment hooks to hook over the upper rim of a pair of spectacles. A wearer of this mask must look through both the lenses of the spectacles and the plastic material in the mask. This particular mask does not protect against liquid materials which may spray or splash over the top of the mask and drop into the eyes.

A visor-supported plastic shield for dentists is illustrated in U.S. Pat. No. 4,701,965 to Landis. Because of the curved surface of the shield, some optical distortion is very likely to occur. Another type of a mask is illustrated in U.S. Pat. No. 3,310,812 to Gaisser. This mask is a flexible sheet of plastic cut in a kidney configuration so that it may be bent about the face with a pair of elastic loops at either side looped over the ears and held in place. This mask does not protect the nose and mouth regions.

Another safety mask is illustrated in U.S. Pat. No. 3,298,031 to Morgan. This mask is a two-part mask in which a pair of goggles similar to ski goggles has a sheet of plastic hinged to the goggles so that the plastic may be pulled down to protect the nose and other facial regions. The plastic sheet has cut-out areas so that the only vision area is through the goggles. The goggles are held on the head by a strap, and there is sufficient room underneath the goggles to permit anyone needing corrective lenses to wear glasses or spectacles underneath the goggles. The plastic shield is pinned on either side of the goggles to form a hinge. The shield may be swung up and down to protect the lower part of the face.

Other face shields are illustrated in patents to Burstyn, U.S. Pat. No. 1,582,164; DuBois, U.S. Pat. No. 2,774,970; Atha, U.S. Pat. No. 2,978,709; and LaRoche, U.S. Pat. No. 1,279,884.

The LaRoche patent illustrates a gauze-type, partial-face mask depending from a pair of spectacles, while the face shield of Atha is a full-face shield having a "window area" in front of the eyes. The Atha shield depends from a carrier headband.

The DuBois shield is a continuous, flexible full-face plastic shield which detachably mounts on a pair of lugs projecting forward of the temples on a spectacle-like frame which holds the shield in place. Vision is through the flexible plastic shield and spectacle frames do not have means for holding lenses.

The Burstyn shield is mounted somewhat similarly to the Atha shield, i.e., to a pair of spectacle temples which are permanently fixed directly to the shield. The Burstyn shield is a partial-face shield which has its upper edge at about eye level of the wearer. A pair of crescent shaped cut-outs (recesses) are made in the upper edge of the shield. Semi-circular frames are permanently mounted to the shield so that lenses of glass may be removably fitted within the semi-circular frames. While the device provides vision through glass lenses, it has temples mounted to the shield and not to the glass lenses which are connected to a bridge and are removable from the shield. Also, the shield does not extend above the eyes. The manner of removing the lenses by pulling them upward from the semi-circular frame would preclude the shield from being simply extended upwardly. The pair of lenses are specially constructed with a lifting bar (bridge) formed in a bow-shape above and between the glass lenses so the lenses could be removed from the shield without removing the shield from the face of the user.

Figure 1:
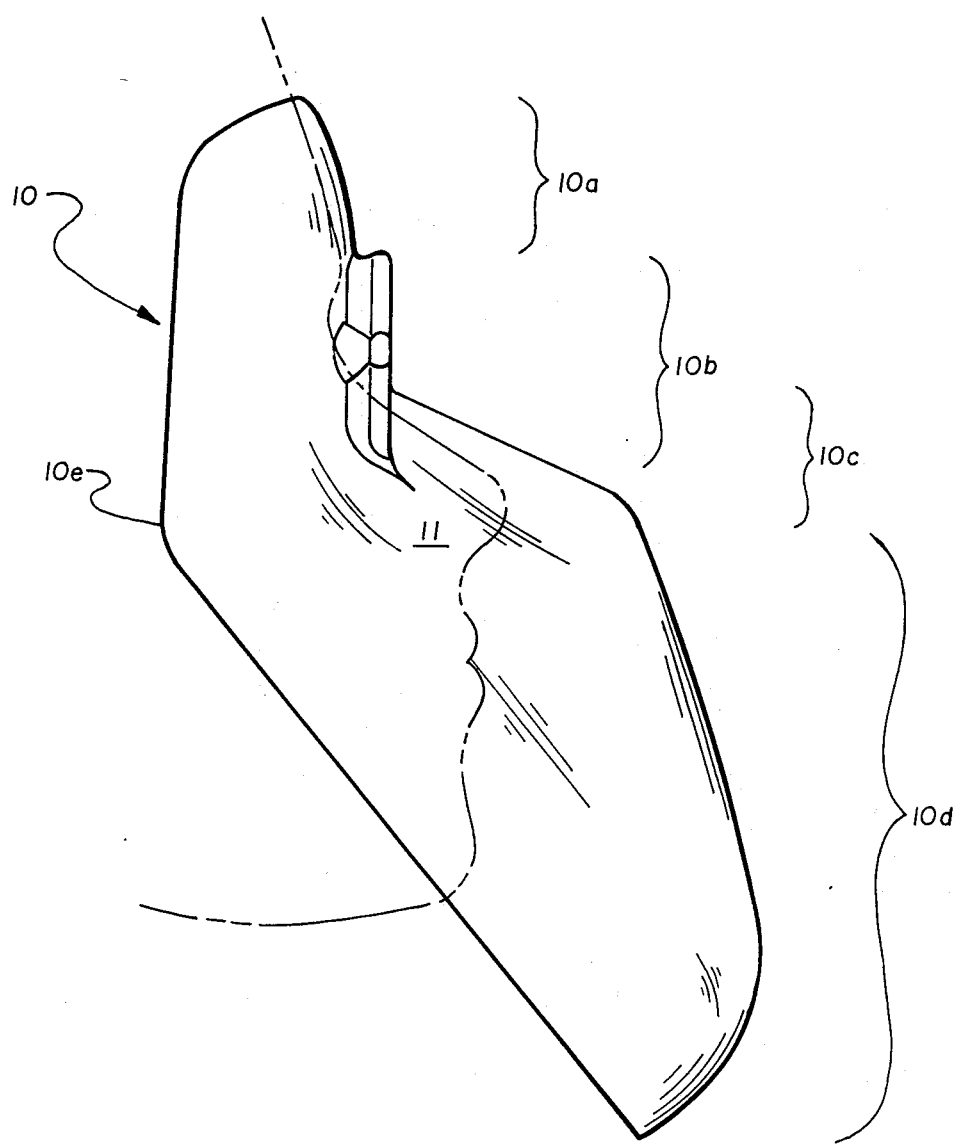
FIG. 1 is a side, elevation view illustrating the profile of the face shield of the instant invention.

The dimensions illustrated on said drawings are generally preferred dimensions which provide a better understanding of the relationship of the individual parts of the face shield These dimensions may, of course, be varied without departing from the basic invention.

DESCRIPTION OF THE INVENTION

A face shield especially useful for dentists and laboratory technicians which is lightweight, generally disposable and readily attached by a generally circular socket arrangement which accepts the rims of spectacles in a press-fit manner has been invented The shield is a full-face shield having a contour for the nose of the wearer. It is a single sheet of very lightweight, thin plastic which is semi-rigid and which has socket-type openings only for the rims of the spectacles which is the sole means by which the shield attaches to a pair of spectacles. Although other openings or apertures could be provided in the shield, for example, nostril openings, it is generally preferred that there be no openings in the facial portion of the shield. Since the shield does not fit tight against the face of a wearer, an adequate air space exists for air to pass between the edges of the shield and the wearer's head so that a wearer may breathe easily.

The shield is very thin, generally being only about 0.10 to about 0.25 millimeters in thickness, with a preferred thickness of about 0.15 to about 0.20 millimeters and is very lightweight, generally weighing only about one-half to about one ounce. While a heavier shield would be effective, a lighter weight is generally preferred. Since the spectacles are the sole support of the shield lightweight shields keeps additional weight to a minimum. A typical pair of spectacles may weigh one to two ounces.

The shield is composed of a front surface and a back surface. The back surface faces the face of a wearer.

The shield is generally concave in shape when viewed towards its back surface with a substantial concave recess or cavity formed in the back surface of the shield to provide a fit over the nose of the wearer.

The edge areas or peripheral margins of the shield, that is, that region which is a short distance inward from the periphery of the shield, are about an inch to about two inches or more, are flared to the rear so that when the shield is worn the shield follows the contours of the forehead, cheeks and chin. The shield peripheral margins are swept backward from the front surface.

As indicated, the only openings in the shield are two eye sockets which are preferably of a predetermined size so that the eye sockets substantially match the peripheral size of the rims of selected pair of spectacles to be worn by the person wearing the mask. Generally, such spectacles will be of a predetermined shape and size so that all shield wearers will preferably wear the same type of spectacles. Many dentists, technicians and so forth require corrective lenses, especially because their work is very intricate and they must have very precise vision to do the work required. Even for dentists and technicians who do not require corrective lenses, it is common practice to wear goggles or safety spectacles of some sort when working in any laboratory. Such are often fitted with lenses without any correction but are lenses with very good optics. Thus, the wearing of spectacles is commonplace among most dentists and technicians and the wearing of a uniform type of spectacle for work purposes does not impose an inconvenience.

The disadvantage of prior art devices having a continuous plastic shield which covers the vision area is that in thin sheets of plastic there will be slight waves and other optical imperfections so that the vision of a dentist, for example, may be impaired or distorted, preventing the clarity of vision required to do the intricate work involved in most dental techniques. Also, if a dentist wears corrective glasses, the presence of another transparent material in front of glasses will tend to cause reflections as well as distortion and distraction.

Thus, it is a significant advantage of the instant invention that there is no plastic sheet over the lenses of the spectacles. Rather, the spectacles are worn by a person wearing the shield, and the shield is held in place by its press-fit of the eye socket openings of the shield over the rims of the spectacles. The socket openings are generally slightly smaller than the rims of the spectacles and the socket flanges preferably have slight grooves therein to receive better the spectacle rims.

Thus, the spectacle sockets of the shield are made with a flange which surrounds the spectacle sockets, projects away from the socket opening from the rear surface a slight distance, and then is bent inward at about 90 degrees to form a land surface against which the front surface of the spectacles may rest. (See FIG. 6) The perpendicular flange, i.e., perpendicular from the main portion of the shield, comes in contact with the outer surfaces of the rims of the spectacles and is sized such that the spectacles must be forced into the socket to form a tight fit. This not only holds the shield in place, but also forms a seal about the spectacles so that a full-face shield is provided to the wearer which covers the forehead so that material may not splash over the top of the spectacles, for example, and down into the eyes. It also has no other openings. Thus, the nose and mouth of the wearer are also protected from having any spray or other material passed into the nose or mouth.

While the plastic sheet may be made of any plastic material such as polyethylene, polypropylene, polymethacrylate, polycarbonate, polyurethane, polyvinyl chloride, polyethylphthylate glycol and the like, it is preferred that the shield be of a clear plastic so that the face of the wearer may be seen. For example, in pediatric dentistry, it may be more comforting for a child to be able to see the face of the dentist rather than seeing an opaque mask descend upon him or her. Also, a clear shield is preferred for the sake of the wearer so that the lighting environment will be substantially the same as when the wearer is not wearing a shield.

Further understanding of the invention may be facilitated by reference to the attached drawings.

The face shield is illustrated in side, elevational view in FIG. 1. The figure is depicted with approximate dimensions for a preferred structure of the face shield. The general profile is somewhat oblate.

The face shield 10 has a forehead region 10a, a spectacle attachment region 10b, a nose region 10c and a mouth-chin region 10d. The upper trailing edge 10e joins the lower trailing edge 10f to form a very wide angled "L". The margins against the shield edge are flared to the rear to provide better protection around the edges. While the flare of the shield margins is extended along the mouth-chin portion of the shield, the shield is angled forward as illustrated in FIG. 1 so that a wearer of the shield will be able to bend his head forward without the bottom edge of the shield immediately hitting his chest, which would tend to dislodge the shield and spectacles from the head of a wearer. Thus, the rear surface of the shield is displaced further from the mouth than it is from the eyes or forehead.

For example, the shield is especially adapted for use by dentists who must be able to bend their heads forward when performing intricate work within a patient's mouth. If the bottom edge of the shield were flared substantially to the rear, then the bottom edge, which is generally located an inch or more below the chin of a wearer, would tend to strike the chest of the wearer in a manner which would limit the amount a wearer could bend his head forward. Any limitations in movement caused by the shield would tend to discourage its use, thereby minimizing its advantage in offering secure protection from spattered liquids.

Generally, the rear surface of the shield is displaced from the nose and mouth of a wearer. The nose portion of the shield is generally far larger than is required for an average sized nose. Thus, the mouth-chin portion of the shield is displaced at least an inch or more from the mouth of a wearer, allowing easy breathing since the flared margins of the shield do not fit against the face or head, thereby allowing a ready air flow to the face of a wearer. Fogging or misting of the spectacles supporting the shield does not occur because of the air flow space.

The shield, as depicted in FIG. 1, has a unique "wide-L" configuration. The lower portion of the shield is not a continuation of the same plane which contains the spectacle socket portion of the shield. The upper portion of the trailing edge and the lower portion of the trailing edge encompass an angle "alpha", which angle is generally from about 135° to about 165°.

So long as the upper trailing edge is parallel to a plane passing vertically through the spectacle sockets, then angle "alpha" is an appropriate way to determine the angulation of the bottom portion of the shield from the upper portion. If the trailing edges (upper and lower portions) are formed as an arc of a circle or an edge approximating the arc of a circle, then the angle beta is a better measurement of angulation. Angle beta also has a range of from about 135° to about 165° with an angle of about 150°±5° being preferable. The vertical axis forming angle beta passes vertically through the spectacle socket while the angled axis is one which represents the forward tilt of the shield.

Another feature of the shield is that the forward tilt of the lower portion of the shield places the rear surface of the shield near the mouth from about two to about four centimeters away from the mouth.

The shield may be foreshortened so that the bottom edge of the shield is closer to the chin and thus does not contact with the chest when the head is bent forward. While such a structure is useful, it does not afford as much protection to the mouth and chin areas and no protection to the exposed neck of the wearer.

Figure 2:
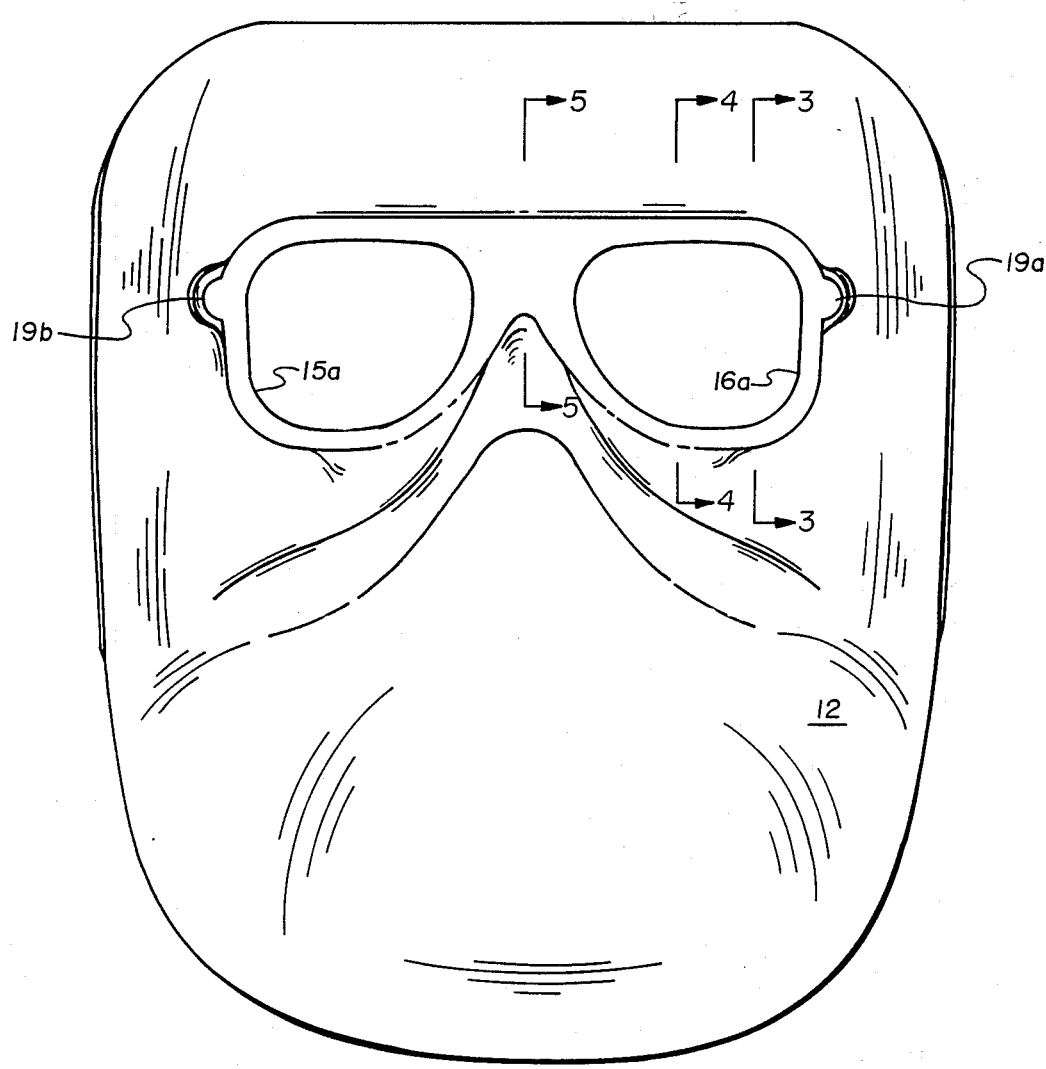
FIG. 2 is a rear elevation view illustrating the facial form of said face shield.

In FIG. 2, a rear, elevational view of the face shield 10 is illustrated. The shield 10, which has somewhat the appearance, shape and size of a full-face mask, has a front surface 11 (See FIG. 1) and a rear surface 12. The central region of the shield, i.e., that portion of the shield directly in front of the eyes, cheeks and mouth, is substantially flat. The marginal (peripheral) region of the shield, i.e., that region which is about one to one and a half inches inward of the peripheral edge 13 of the shield, is flared to the rear to protect the eyes and mouth especially from liquids or materials sprayed or propelled towards the front of the shield.

The shield has a nose region 14 which is recessed from the rear surface. The nose region extends into a large, bulbous area on the front surface of the shield which forms the mouth-chin regions of the shield. The only openings or cut-out areas in the shield are the two spectacle (glasses) sockets 15 and 16. These sockets are slightly under-sized and formed to accept and hold firmly the rims surrounding the optical lenses of a pair of spectacles.

Figure 6:
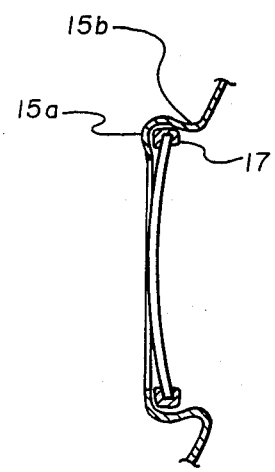
FIG. 6 is a partial sectional view along section lines 3—3 illustrating the gripping action of the socket portion of the shield on that portion of spectacle frames which encompass a lens.

The views presented in FIGS. 2, 3, 4, 5 and 6 illustrate the interaction of the face shield 10 and a pair of spectacles (FIG. 6). In FIG. 2, which is an elevational rear view, the spectacle sockets 15 and 16 are shown with flanges 15a and 16a recessed slightly from the rear surface 12. The flanges 15a and 16a form stops for the spectacle rims 17 and 18 when the spectacles are inserted into the shield from the rear.

Figure 7:
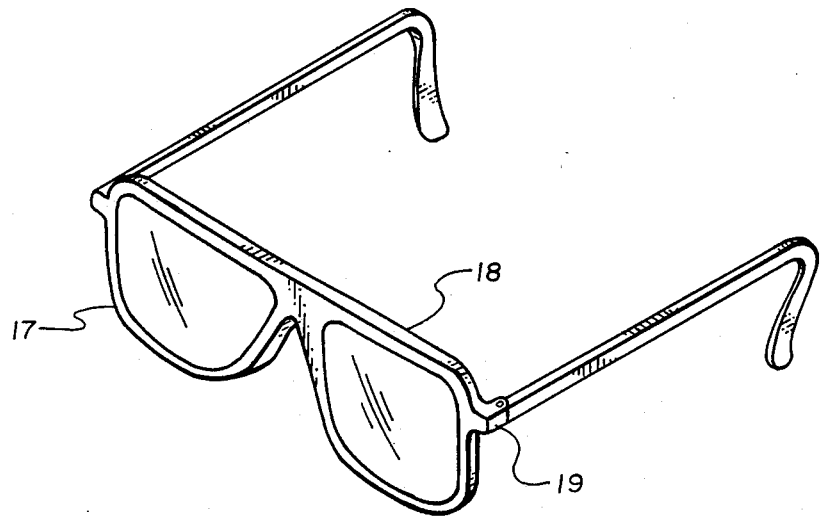
FIG. 7 is a perspective view of a pair of spectacles useful in coacting with a face shield of the instant invention in a form-fit manner to secure said shield to said spectacles frame.
Figure 8:
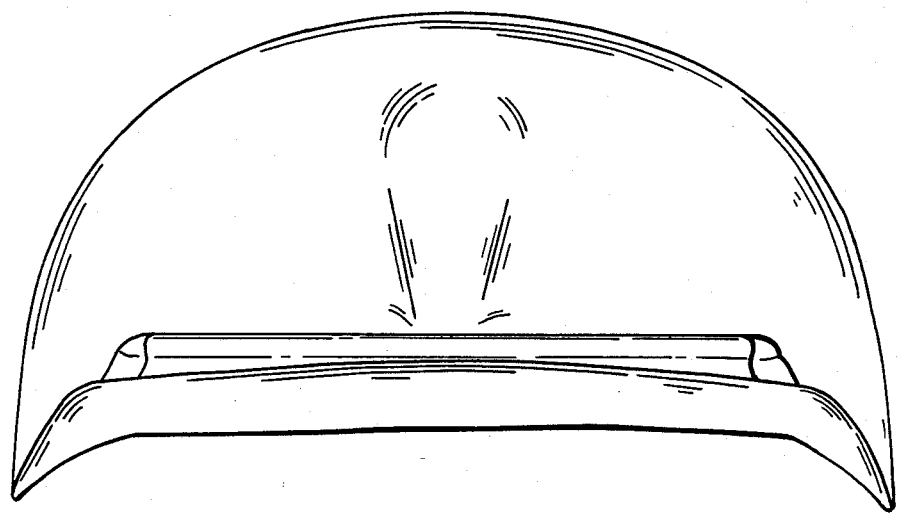
FIG. 8 is a plan, top view illustrating a profile of the face shield when viewed from above.

The sockets 15 and 16 are sized to be substantially the same shape, but preferably sized about two to four mils smaller than the outer peripheral surface of rims 17 and 18 which surround the lenses of the spectacles of FIG. 7. The manner of attachment is illustrated in FIGS. 3, 4, 5 and 6. The shield socket 15 is formed by circular flange 15a and shield socket shoulder 15b.

Figure 3:
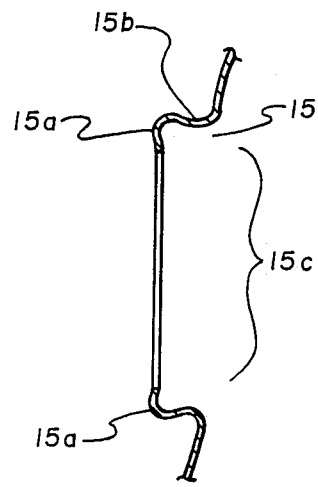
FIG. 3 is a partial sectional view of the spectacle socket portion of the shield along section lines 3—3.
Figure 4:
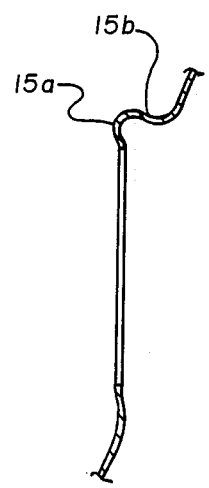
FIG. 4 is a partial sectional view of the spectacle socket portion of the shield along section lines 4—4.
Figure 5:
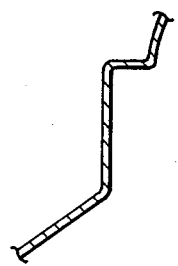
FIG. 5 is a partial sectional view of the shield above the bridge of the nose portion along section lines 5—5.

The force fit of rim 17 into socket 15 is illustrated in FIG. 6 wherein the outer surface of rim 17 fits snugly within shoulder 15b and the front surface of rim 17 fits against the peripheral flange 15a. The region between shoulder 15b and flange 15a is illustrated in FIG. 3,4 and 6 as having a slight groove because of shoulder 15b. In particular, the outer edges of the rims, including the temple hinges, bind securely within the socket openings. The recesses 19a and 19b hold securely the temple hinges of the spectacles shown in FIG. 7 in a press-fit manner.

Generally, the lateral distances between the outboard surface of the temple hinges of the spectacle is slightly greater than the maximum distance between the recessed surfaces 19a and 19b. This is also true of the outboard edges of the spectacle rims, i.e., the maximum lateral distance of the spectacles is slightly greater than the maximum distance between the outboard vertical surfaces of the spectacle sockets.

A pair of spectacles useful in coacting with the face shield of the instant invention is illustrated in FIG. 7. The spectacles preferably have plastic rims 17 and 18 completely surrounding the optical lenses. Such full circumferencing rims provide a good force fit with the spectacle sockets of the face shield. The concave shape of the face shield may also help to hold the shield in place since the outboard margins of the rims contact the outboard margins of the sockets. Thus, if the lateral distance between the outboard margins of the spectacle rims is slightly greater than that of the sockets, the shield may deform slightly to admit the spectacles and thereby apply another force which tends to hold the shield onto the spectacles.

The face shield of the instant invention is particularly unique in that it is a full-face shield which virtually ensures the wearer complete protection from any spattering liquids in front of his face.

Other unique features of the shield are its form-fit to a pair of spectacles which provide excellent optics and the sole means by which the shield is secured to the head of a wearer. The shield further has overlapping flanges about the optical lenses of the spectacles to form a sufficient seal to prevent spattering liquids to penetrate the spectacles-shield barrier.

Although the shield is full-faced, it is very light and readily carried by the spectacle temples without any discomfort to a shield wearer. Furthermore, the forward rake of the mouth-chin region permits a wearer to bend his head forward without the lower edge of the shield contacting the chest or neck prematurely. The chin and mouth are, however, protected by the shield since the lower edge of the shield generally projects a significant distance below the chin of a wearer.

Another advantageous feature of the shield is its light weight and simple construction which permits the shield to be disposable. Since an optical grade plastic is not required and the forming techniques are routine and straightforward, the shield may be inexpensively constructed. The shields, however, can be washed, sterilized and reworn.

Also, because the shield need not have good optical characteristics, it may be very thin and lightweight, which allows it to be readily held upon a pair of spectacles by a force-fit.

Furthermore, the lightweight nature of the shield allows a person wearing the shield to bend his head forward with the shield causing the spectacle to be pulled forward by gravity and dislodged.

Another feature of the shield which makes it especially useful for dentists is its generally wide "L" shape which has the lower portion of the shield tilted forward so that when a shield wearer bends his head forward the lower edge of the shield does not prematurely touch the neck or chest of a wearer. Such premature contact could, of course, dislodge the shield or spectacles from the head of a wearer.

The face shield is made of lightweight, thin plastic sheet material which can be readily vacuum formed into the face shield shape. The contour of the shield, including the nose depression and shield sockets may be formed in one operation from one continuous sheet of plastic. The opening 15c (and 16c) may be readily punched out (cut-out) in a single, second step to complete formation of the finished shield.

Although other forming techniques may be used, vacuum forming of thin thermoplastic sheets is generally preferred. Also, it is generally preferred that the plastic be clear. Also, a thermoset plastic shield may be made by utilizing a formable B-shape resin which may be placed in a mold and heated to complete curing to form a semi-rigid, thermoset plastic shield.

What is claimed is:

1. A full-face protective shield comprising a very lightweight plastic full-face shield formed from a thin substantially continuous sheet of plastic having a pair of spectacle socket apertures, said shield having facial contours with a concave recess in the rear surface for the nose and curved peripheral edges flared to the rear to fit under the chin and to follow the contour of the forehead and cheeks, said pair of spectacle socket openings in said shield being adjacent the upper portion of the nose recess and sized to fit entirely around the lens rim portion of a spectacle frame to support the shield and to form a substantial seal between the shield and the spectacles so that the shield in conjunction with the lenses of the spectacles covers the eyes, nose, forehead, cheeks, mouth and chin of the wearer with a substantially continuous surface.

2. The shield of claim 1 wherein the shield has a thickness of from about 0.10 to about 0.25 millimeters in thickness.

3. The shield of claim 1 wherein said plastic is transparent.

4. The shield of claim 1 wherein said spectacle socket apertures form a force-fit relationship with at least the outboard portions of the spectacle rims which are adjacent to the temple hinges.

5. The shield of claim 1 wherein the weight of said shield is less than about one ounce.

6. The shield of claim 1 wherein the lower portion of the shield is spaced further away from the face of a wearer than the upper portion of the shield.

7. The shield of claim 1 wherein circumscribing flanges around the front of said spectacle socket apertures overlap the rims of said spectacles when the spectacles and shield are fitted together.

8. The shield of claim 1 wherein said spectacle socket apertures have a slight rim-receiving groove in at least the outboard portions of said socket apertures.

9. The shield of claim 1 wherein the trailing edge of the lower portion of the shield is at a substantial obtuse angle to the trailing edge of the upper portion of the shield.

10. The shield of claim 1 wherein the spectacle socket apertures are sized to fit a preselected pair of spectacles.

11. The shield of claim 10 wherein said spectacles have rims surrounding the lenses of said spectacles.

12. The shield of claim 1 wherein said spectacle socket apertures have a recessed groove encircling at least a portion of said spectacle socket openings, said groove sized to receive the rims of the spectacles in a force-fit manner to secure the shield to the spectacle rim.

* * * * *